Aug. 4, 1970 R. S. MOORE Plant Pat. 2,988
MINIATURE ROSE PLANT
Filed Sept. 6, 1968
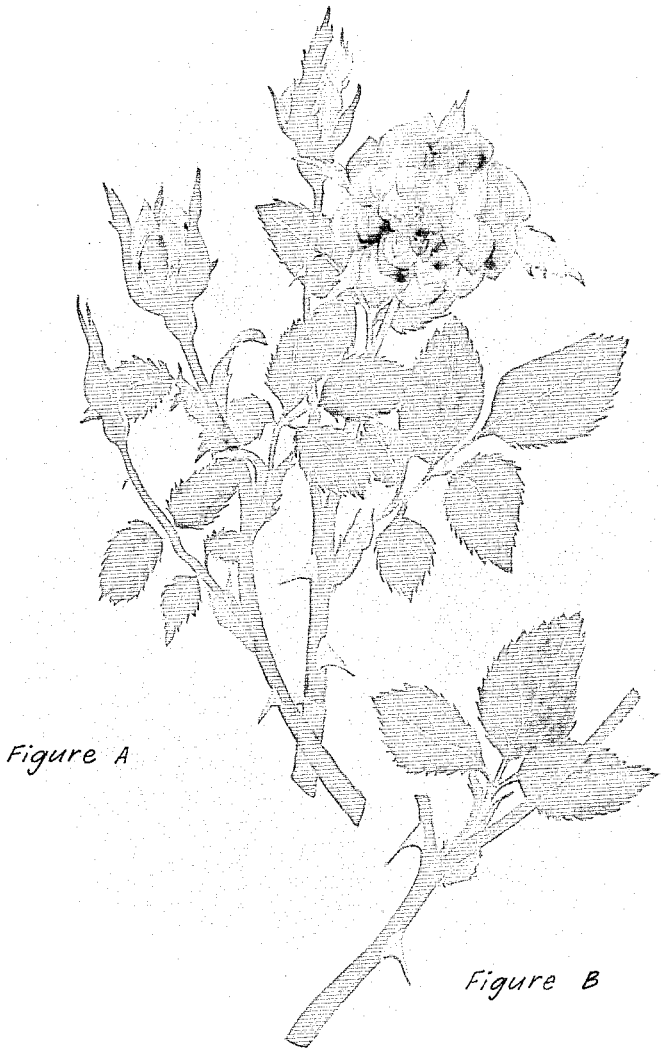
WITNESS
Jeanette Nunn Copley
INVENTOR
Ralph S. Moore

United States Patent Office

Plant Pat. 2,988
Patented Aug. 4, 1970

2,988

MINIATURE ROSE PLANT

Ralph S. Moore, 2519 E. Noble Ave.,
Visalia, Calif. 93277

Filed Sept. 6, 1968, Ser. No. 758,165
Int. Cl. A01h *5/00*
U.S. Cl. Plt.—10 1 Claim The present invention relates to a new and distinct variety of hardly, dwarf, bush type rose plant of the hybrid miniature class; the variety being primarily characterized—as to novelty—by very double red flowers which are similar to Little Buckaroo (Pat. 1,726) except that they are more double, deeper red color and its petals have a harder, more firm, texture.

The variety is further characterized by:

An abundance of bloom, with flowers on mature plants usually borne in clusters of three to five or more to the stem.

A plant which is vigorous, of rounded habit, but which, in its younger stage, may tend to grow more spreading than tall, with glossy, dark green leaves. The plant, which has a normal average height of about 16"–18" at maturity, resembling the general plant habit of Little Buckaroo (Pat. 1,726) miniature rose.

A plant which grows and blooms satisfactorily outdoors in pots or in the garden; and provides long lasting cut flowers.

The present variety of miniature rose was originated by me in my nursery located at Visalia, Calif., under conditions of careful control and observation, as a cross of an unnamed and unpatented seedling of complex breeding as the seed parent × Little Buckaroo as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color identifications being by reference to the British Colour Council Colour Chart, except where common terms of color definition are employed.

Type: Hardy; medium dwarf; bush; seedling; outdoors; garden decoration; cut flowers.

Class: Hybrid miniature.

Flowers:

*Continuity.*—Continuous repeat bloom during normal growing season.

*Fragrance.*—Slight.

Flowers borne: Singly on young plants; usually several together in cluster, on medium length sturdy stem, on mature plants.

Quantity of bloom: Average abundance.

Bud: Peduncle—medium length; sturdy and somewhat heavier than the type; erect; medium to dark green.

Before calyx breaks: Size—small. Form—short pointed (almost round with pointed tip). Usually with numerous short hair-like appendages on surface of the bud; with foliaceous parts extending beyond the tip of the bud equal to one-half or more of its length.

*Color.*—Medium green.

*As first petal opens.*—Size—small.

*As calyx breaks.*—Color—dark red.

*Form.*—Short pointed. Color: outside—Chrysanthemum Crimson 824/2 shading lighter toward the base; inside—Cardinal Red 822/1 overlaid with blackish tones, shading to near white at base.

*Opening.*—Usually opens well and rather slowly.

Bloom:

*Size when fully open.*—Small—about 1¼".

*Petalage.*—Very double—varies with the season but averages 40 or more; sometimes 60 or more.

*Form.*—High centered and full at first, with outer petals at right angle in reference to stem, and later at maturity outer petals rolled downward giving flower somewhat of a ball shape.

Petals: Very thick and firm; velvety on upper surface; sanity on lower surface.

*Shape.*—Outside petals—broad lanceolate (almost round); intermediate—broad lanceolate with nearly round tip; inside—lanceolate (usually with rounded tip).

*Color.*—Newly opened flower from plant grown outdoors (September 1968), Visalia, Calif. Outside petal: outside surface—Chrysanthemum Crimson 824/2 with darker and lighter tones, shading into a small near white area at base; inside surface—Currant Red 821/2 overlaid with blackish tones and shading into near white at base. Intermediate petal: outside surface—Chrysanthemum Crimson 824/3 with darker tones and shading into near white at base; inside surface—Currant Red 821/1 overlaid with blackish tones and shading into near white at base. Inner petal: outside surface—Chrysanthemum Crimson 824/2 with darker and lighter tones and whitish area at base; inside surface—same as intermediate petal.

*General color effect.*—Newly opened flower—deep velvety red. Three days open—deep red (color often deepens as flowers age).

*Behaviour.*—Hang on for a time.

*Flower longevity (May-June 1968).*—Bush in garden—5–7 days or longer. Cut flowers kept at living room temperature—4–7 days.

Reproductive organs:

*Stamens.*—Few to none.

*Anthers.*—Few to none.

*Pollen.*—Small amount at times.

*Pistils.*—Moderate number.

*Styles.*—Uneven, relatively long, bunched.

*Stigma.*—Usually well formed and functional.

*Ovaries.*—All enclosed in calyx.

*Hips.*—Few, round, greenish to orange, few seeds.

Foliage:

*Leaves.*—Compound of 5 (sometimes 7) leaflets; abundant, medium small, leathery, glossy.

*Leaflets.*—Shape—lanceolate; apex acute, base round. Margin—serrate. Color—medium to dark green; new leaves sometimes tinted reddish or bronze along serrated margin.

*Rachis.*—Strong; upper surface grooved with a few short hiars or prickles; under side sparsely thorny.

*Stipules.*—Medium to long; medium width; medium length points, turning out at an angle of 45 degrees or more.

Growth:

*Habit.*—Compact; bushy; moderately spreading; much branched.

*Growth.*—Vigorous. Canes—medium to strong, stocky. Main stem: color—medium to dark green. Thorns—moderately thorny; long oval base; medium length; hooked slightly downward. Color—brown. Prickles—none. Hairs—none.

*Branches.*—Color—medium green. Thorns—moderately thorny; medium length; hooked slightly downward; long oval base; color—reddish to brown.

*New shoots.*—Color—medium to bright green, sometimes lightly tinted reddish. Thorns—moderately thorny; medium to long, slender; hooked slightly downward; long oval base. Color—reddish. Prickles—none. Hairs—none.

The miniature rose plant and its flowers as herein described may vary slightly in detail due to climatic, soil and cultural conditions under which the variety may be grown; the present description being of the variety as grown at Visalia, Calif.

The following is claimed:

1. A new and distinct variety of miniature rose plant of hardy, moderately dwarf, rounded (or slightly spreading), much branched, bush type, as illustrated and described, characterized by buds and flowers resembling the Little Buckaroo (Pat. 1,726) miniature rose in color and general effect but with more double flowers, the petals of which have a firmer texture and the color being a darker red; the bush being more spreading when young and the foliage harder textured; and further characterized by a plant which is vigorous in growth, yet compact, easy to propagate from cuttings, with small to medium size, medium to dark green, foliage, an abundance of bloom, with flowers usually borne several to the stem (on mature plants) in compact well arranged clusters.

No references cited.

ROBERT E. BAGWILL, Primary Examiner